United States Patent
Bastioli et al.

(10) Patent No.: US 7,812,186 B2
(45) Date of Patent: Oct. 12, 2010

(54) PROCESS FOR THE PRODUCTION OF DERIVATIVES OF SATURATED CARBOXYLIC ACIDS

(75) Inventors: Catia Bastioli, Novara (IT); Tiziana Milizia, Novara (IT); Giampietro Borsotti, Novara (IT)

(73) Assignee: Novamont S.p.A., Novara (IT)

( * ) Notice: Subject to any disclaimer, the term of this patent is extended or adjusted under 35 U.S.C. 154(b) by 57 days.

(21) Appl. No.: 12/067,343

(22) PCT Filed: Sep. 21, 2006

(86) PCT No.: PCT/EP2006/066610

§ 371 (c)(1),
(2), (4) Date: Mar. 19, 2008

(87) PCT Pub. No.: WO2007/039481

PCT Pub. Date: Apr. 12, 2007

(65) Prior Publication Data

US 2008/0245995 A1     Oct. 9, 2008

(30) Foreign Application Priority Data

Sep. 23, 2005   (IT) .......................... MI2005A1779

(51) Int. Cl.
*C07C 51/16* (2006.01)
(52) U.S. Cl. ...................... 554/138; 554/123; 554/124; 554/135; 554/136
(58) Field of Classification Search ................. 554/132, 554/134, 135, 136, 138
See application file for complete search history.

(56) References Cited

FOREIGN PATENT DOCUMENTS

| WO | WO-94/10122 | 5/1994 |
| WO | WO9410122 | * 5/1994 |

OTHER PUBLICATIONS

Santacesaria et al: "Oxidative Cleavage of the Double Bond of Monoenic Fatty Chains in Two Steps: A New Promising Route to Azelaic Acid and Other Industrial Products"; Industrial & Engineering Chemistry Research, Jun. 27, 2000, 39(8), 2766-2771.
Antonelli et al.: "Efficient Oxidative Cleavage of Olefins to Carboxylic Acids with Hydrogen Peroxide Catalyzed by Methyltrioctylammonium Tetrakis(oxodiperoxotungsto)phosphate(3-) under Two-Phase Conditions. Synthetic Aspects and Investigation of the Reaction Course"; Journal of Organic Chemistry, Sep. 22, 1998, 63(21), 7190-7206.

* cited by examiner

*Primary Examiner*—Deborah D Carr
(74) *Attorney, Agent, or Firm*—Connolly Bove Lodge & Hutz LLP

(57) ABSTRACT

A process for the production of carboxylic acids and their derivatives comprising the steps of: (c) reacting a derivative of an unsaturated fatty acid with an oxidizing compound in the presence of a catalyst capable of catalysing the reaction of oxidation of the double olefinic bond of the derivative of the unsaturated fatty acid so as to obtain as intermediate product of reaction a vicinal diol; and (d) reacting said intermediate compound with oxygen, or a compound containing oxygen, in the presence of a catalyst capable of catalysing the reaction of oxidation of the hydroxyl groups of the vicinal diol to carboxylic groups, characterized in that both of the steps (a) and (b) are carried out in the absence of added organic solvent and in that the water/diol ratio in the reaction of step (b) is less than 1:1.

31 Claims, No Drawings

PROCESS FOR THE PRODUCTION OF DERIVATIVES OF SATURATED CARBOXYLIC ACIDS

RELATED APPLICATIONS

This application is a national stage application (under 35 U.S.C. §371) of PCT/EP2006/066610 filed Sep. 21, 2006, which claims benefit of Italian application MI2005A001779 filed Sep. 23, 2005, disclosure of which is incorporated herein by reference.

The present invention relates to a process for the production of saturated carboxylic acids and their derivatives, comprising the steps of:

(a) reacting a derivative of an unsaturated fatty acid with an oxidizing compound in the presence of a catalyst capable of catalysing the reaction of oxidation of the double olefinic bond of the derivative of the unsaturated fatty acid so as to obtain, as intermediate product of reaction, a vicinal diol; and (b) reacting said intermediate compound with oxygen, or a compound containing oxygen, in the presence of a catalyst capable of catalysing the reaction of oxidation of the two hydroxyl groups of the vicinal diol to carboxylic groups.

A process of the type mentioned above is defined as oxidative scission of the unsaturated fatty acids. In the course of the first reaction an intermediate is formed that is a vicinal diol in which two hydroxyl groups are bound to the carbon atoms that initially were bound by a double olefinic bond.

Processes of oxidative scission of fatty acids and of their derivatives, such as, for example, esters of fatty acids are known in the literature. For example, a process of the type mentioned above is described in the patent No. EP-0 666 838. In said patent, the process of oxidative scission is characterized in that both of the steps (a) and (b) are carried out in the absence of any added organic solvent and in that, in the course of step (b), water is added to the reaction mixture resulting from the reaction of step (a) so as to obtain a water/diol ratio comprised between 1:1 and 5:1, before reacting the mixture with oxygen, or a compound containing oxygen, in the presence of a cobalt compound as catalyst.

This process does not entail any purification of the intermediate product of reaction (vicinal diol) and does not entail the addition of solvents for the purpose of carrying out the oxidation of the diols that is performed in the presence of water. The characteristics of the intermediate that is formed at the end of the first step, in particular its high viscosity, render, however, necessary the addition of large amounts of water to enable the second step of the process to be carried out.

From the standpoint of industrial production, this fact is particularly disadvantageous since it involves the need to have reactors with large volumes. Furthermore, at the end of the process, given the large amount of residual water present, the treatments both for the recovery of the catalysts dissolved therein and for its subsequent disposal linked to the presence of organic residue, are particularly burdensome.

Lastly, the mixtures obtained according to the patent No. EP 0 666 838 present a pasty, greasy and pitchy texture.

For the purpose of overcoming these drawbacks, as well as other disadvantages that will be clarified in the course of the ensuing description, the process described in the present invention has been developed.

With the process according to the present invention it is in fact possible to produce saturated carboxylic acids and their derivatives starting from derivatives of unsaturated fatty acids without any need to add significant amounts of water in step (b) of the reaction of oxidative scission if not the modest amounts of water of the solution in which the catalyst is dissolved.

The present invention relates to a process for the production of saturated carboxylic acids and their derivatives comprising the steps of:

(a) reacting a derivative of an unsaturated fatty acid with an oxidizing compound in the presence of a catalyst capable of catalysing the reaction of oxidation of the double olefinic bond of the derivative of the unsaturated fatty acid so as to obtain as intermediate product of reaction a vicinal diol; and (b) reacting said intermediate compound with oxygen, or a compound containing oxygen, in the presence of a catalyst capable of catalysing the reaction of oxidation of the hydroxyl groups of the vicinal diol to carboxylic groups, said process being characterized in that both of steps (a) and (b) are carried out in the absence of added organic solvent and in that water is not added to the reaction mixture resulting from step (a) during step (b), except for the water of solution in which the catalyst is dissolved, so as to obtain a water/diol ratio of less than 1:1, preferably less than 0.7:1 and most preferably less than 0.5:1.

By derivative of an unsaturated fatty acid is understood an unsaturated fatty acid in which the carboxylic group has been made to react so as to prevent, or in any case minimize, any possible reactions of the carboxylic group thus modified in the course of the process.

The fatty acid can be either mono-unsaturated or poly-unsaturated. Examples of unsaturated fatty acids are 9-tetradecenoic acid (myristoleic acid), 9-hexadecenoic acid (palmitoleic acid), 9-octadeceneoic acid (oleic acid), 12-hydroxy-9-octadeceneoic acid (ricinoleic acid), 9-icosenoic acid (gadoleic acid), 13-docosenoic acid (erucic acid), 15-tetracosenoic acid (nervonic acid), 9,12-octadecadienoic acid (linoleic acid), and 9,12,15-octadecatrienoic acid (linolenic acid).

Also mixtures of the derivatives of unsaturated fatty acids, such as for example the ones present in vegetable oils such as soybean oil, olive oil, castor oil, sunflower oil, peanut oil, rape-seed oil, corn oil, palm oil, etc. can be used.

Particularly advantageous is the use of mono-unsaturated fatty acids. Particularly preferred are oleic acid and erucic acid, particularly their esters, the most advantageous being the use of methyl esters.

The carboxylic group of the unsaturated fatty acid can be modified by means of reaction with an alcohol (to yield an ester), an amine (to yield an amide), etc. In the case of esterification the ester group comprises preferably a C1-C9 alkyl group, more preferably methyl, ethyl, propyl. Particularly preferred is methyl oleate in particular the one obtained by transesterification of methanol with the triglycerides contained in sunflower oil with a high content of oleic acid.

The oxidizing substance used for carrying out step (a) of the process according to the invention is preferably an aqueous solution of hydrogen peroxide in concentrations comprised between 30% and 70%, preferably between 35% and 60% and even more preferably between 40% and 49.9%.

Advantageously, the catalyst of step (a) belongs to the group consisting of tungsten and molybdenum, particularly their acids and alkaline salts thereof. Said catalyst is present in an amount comprised between 0.03 wt % and 2 wt %, more preferably between 0.07 wt % and 1.8 wt % and still more preferably between 0.08 wt % and 1.5 wt % with respect to the derivative of the unsaturated fatty acid.

In order to improve the dispersion of the catalyst into the reaction mixture, a dispersing agent such as a surfactant (belonging to the classes of anionic, cationic, non-ionic and zwitterionic surfactants) can be advantageously added.

As regards the catalyst of step (b), it belongs advantageously to the class of cobalt-based compounds, such as for example cobalt acetate, cobalt chloride and cobalt sulphate or their mixtures, used in an amount comprised between 0.1 mol % and 3 mol %, preferably between 0.2 mol % and 2 mol %, and more preferably between 0.3 mol % and 1.5 mol %, with respect to the diol produced in step (a).

As catalyst of step (b), compounds of tungsten and molybdenum, and their acids and alkaline salts, can be added to the cobalt-based compounds preferably in an amount up to 2 mol % respect to the diol.

In a preferred embodiment of the process according to the invention, at the start of step (a) a small addition of the intermediate that is to be formed at the end of step (a) itself is used (the so-called <<reaction foot>>) in so far as the initial presence of the intermediate that is to form favours the activation of the reaction.

The "reaction foot" can be preferably added in an amount $\leqq 5\%$, more preferably $\leqq 3\%$ by weight.

Advantageously, in the case where the <<reaction foot>> is not available, it is useful to add to the initial reaction mixture a certain amount of $H_2O_2$ and to wait for the temperature to increase as a result of the exothermia of the process. When this occurs, it means that the reaction of the unsaturated fatty acid with $H_2O_2$ has occurred, and hence the dihydroxide that activates the reaction is formed.

In a preferred embodiment of the process according to the invention, in the course of step (a) nitrogen is made to flow to distil a part of the water produced in the process. In this way, an excessive dilution of $H_2O_2$ is prevented.

In a preferred embodiment of the process according to the invention, at the end of step (a), the water present in the reaction mixture and the catalyst dissolved therein are removed. The catalyst is then recovered by means of known techniques. In the case where tungstic acid is used it is possible, for example, to concentrate the waters (distilling a part thereof) and then acidify with hydrochloric acid to precipitate the tungstic acid. It is thus possible to recover the catalyst, which can thus be reused for subsequent reactions.

The elimination of the water at the end of step (a) also presents a further advantage. The catalyst of step (a) can in fact be present in the course of step (b) of the process, together with the addition of the catalyst necessary for this second step of the process. With elimination of the water at the end of step (a) and of the catalyst dissolved therein, it becomes in fact possible to add the two catalysts in the stoichiometric ratios necessary for optimizing execution of step (b).

The reaction temperature of the present process is comprised between 50° C. and 90° C. The time necessary for carrying out the reaction of step (a) of the present process is comprised between 2 and 10 hours, whilst the time necessary for carrying out step (b) is comprised between 3 and 12 hours.

The process according to the invention can advantageously be carried out at atmospheric pressure or in any case at low pressures ($\leqq 20$ atm, preferably $\leqq 15$ atm and more preferably $\leqq 10$ atm), so proving particularly advantageous from the standpoint of industrial production. Different from the end result of the process described in the patent No. EP 0 666 838, which is a pasty and greasy mixture, the end result of the process described according to the present invention, is a clear oil comprising the derivative of a dicarboxylic acid, a monocarboxylic acid, as well as a series of esters of the vicinal diol formed at the end of step (a). In the case where the derivative of the starting fatty acid is pure methyl oleate, said oil consequently comprises the monomethyl ester of azelaic acid (monomethyl ester of the diacid formed by oxidative scission), pelargonic acid, as well as a series of esters of the methyl ester of dihydroxystearic acid with monomethyl azelate and/or pelargonic acid.

The individual components can then be purified using techniques that exploit the different solubility in water of the products obtained and of the various derivatives and/or using processes of distillation and in any case using conventional techniques.

Before starting the purification process cited above it can be useful to esterify the mixture as a whole or the acids therein contained.

Said oil can in any case be used just as it is or else constitute raw material to form a lubricating oil or a biodiesel or an intermediate of reaction for pre-polymers.

EXAMPLES

Example 1

Step (a) (Reaction with $H_2O_2$)

There were introduced into a reactor:

1000 g of crude methyl oleate (methyl esters from sunflower oil with an extremely high content of oleic acid: 92% methyl oleate; 1% methyl linoleate; 4% methyl palmitate; 3% methyl stearate)

10 g of tungstic acid 50 g of crude methyl dihydroxystearate (the intermediate obtained at the end of step (a) coming from a preceding reaction, the so-called <<reaction foot>>).

The temperature was increased to 65° C., and 250 cc of 49.9% $H_2O_2$ solution were added in 3 h. In the course of the reaction, nitrogen was made to flow to distil a part of the water produced in the process. Approximately 70 cc of water were distilled in the course of the 3 h. Once addition of $H_2O_2$ had been completed, approximately 7 g of sodium bicarbonate dissolved in 100 cc water were added to convert tungstic acid into tungstate, which is more soluble in water, and the aqueous phase was separated when hot (at approximately 60° C.) from the organic phase. Approximately 150 g of aqueous solution containing the catalyst were thus separated, and approximately 1150-1200 g of oily phase were obtained. Of this oily phase 50 g were set aside as "reaction foot" for the subsequent reaction.

The oily phase contained 75-80% of methyl dihydroxystearate, a small amount of $H_2O_2$ (1-2%), palmitate and stearate, which do not participate in the reaction, methyl 9,10-epoxystearate, which is an intermediate of reaction, pelargonic acid and monomethyl azelate, which already start to form in this reaction step, and acetals that derive from secondary reactions.

Step (b) (Reaction with $O_2$)

Added to the oily phase was an aqueous solution of catalyst prepared in the following way: (for 1150 g of oily phase)

15.1 g of $Na_2WO_4$ were dissolved in 200 cc of water.

6.9 g of $CoAc_2$ (0.03 mol) were dissolved in 100 cc of water.

The two solutions were mixed, with consequent precipitation of cobalt hydroxide. Co(II) was then oxidized to Co(III) by means of addition of a stoichiometric amount of $H_2O_2$. By means of addition of HCl, the product was then acidified to obtain pH=3, in this way solubilizing the dark-green precipitate. The product was finally brought up to volume with 400 cc of distilled water.

The temperature was then raised to about 75-80° C., and $O_2$ was then bubbled through at a rate of 30 lt/h. The reaction lasted approximately 5-6 h. Start of oxidation was detected by the change of colour of the catalytic solution from green to yellow.

At the end of the reaction the aqueous phase containing the catalyst was separated when hot, to be recycled in the subsequent steps.

The oily phase (slightly more than 1150 g) comprised pelargonic acid, monomethyl azelate, small amounts of azelaic acid and dihydroxymethylstearic acid that has not reacted, methyl palmitate and methyl stearate present in the esters right from the start, and mixtures of mono-esters and di-esters of methyl dihydroxystearate with pelargonic and monomethyl azelate.

The oily phase was treated with sodium carbonate or ammonia to transform the monomethyl azelaic acid and pelargonic acid into the corresponding water-soluble salts of sodium or ammonium. The two salts were separated from the residue by addition of water.

From 1150 g of product of the reaction approximately 300 g of residue and approximately 850 g of mixture of acids were obtained. By subsequent distillation of the mixture of the acids, approximately 350 g of pelargonic acid and 450 g of monomethyl azelate were obtained.

The above result corresponds to a yield of approximately 70% for both of the products.

Example 2

Step (a)

There were introduced into a reactor:

1000 g of crude methyl oleate (methyl esters from sunflower oil with high content of oleic acid: 84% methyl oleate; 9% methyl linoleate; 4% methyl palmitate; 3% methyl stearate)

10 g of tungstic acid 50 g of crude methyl dihydroxystearate (the intermediate obtained at the end of step (a) coming from a preceding reaction, the so-called <<reaction foot>>)

The temperature was increased to 60-62° C., and 250 cc of 49.9% $H_2O_2$ solution were added in 3 h. The reaction was carried out as described in the example 1.

After salification of tungstic acid with a sodium bicarbonate solution, the aqueous phase, containing tungstate, was separated, while the organic phase (approximately 1150 g of oily phase), containing 70-75% of methyl dihydroxystearate, was ready for the subsequent oxidative step.

Step (b)

Added to the organic phase was an aqueous solution of salts of Co (II) as catalyst (5 g $CoCl_2$ 6 $H_2O$ (0.02 mol) in 400 cc of distilled water).

The temperature was maintained to about 75-80° C., and $O_2$ was then bubbled through at a rate of 30 lt/h for 6 h.

At the end of the reaction the aqueous phase containing the catalyst was separated when hot, to be recycled in the subsequent steps.

Approximately 1150 g of oily phase are obtained which essentially consist of pelargonic acid and monomethyl azelate in a quantity corresponding to a yield of approximately 65-70% for both of the products.

The invention claimed is:

1. Process for the production of saturated carboxylic acids and their derivatives, comprising the steps of (a) reacting a derivative of an unsaturated fatty acid with an oxidizing compound in the presence of a catalyst capable of catalysing the reaction of oxidation of the double olefinic bond of the derivative of the unsaturated fatty acid so as to obtain as intermediate product of reaction a vicinal diol; and (b) reacting said intermediate compound with oxygen, or a compound containing oxygen, in the presence of a catalyst capable of catalysing the reaction of oxidation of the hydroxyl groups of the vicinal diol to carboxylic groups, said process being characterized in that both of the steps (a) and (b) are carried out in the absence of added organic solvent and in that the water/diol ratio in the reaction of step (b) is less than 1:1.

2. Process according to claim 1, wherein at the end of step (a), the water present in the reaction mixture and the catalyst dissolved therein are removed.

3. Process according to claim 2, wherein an aqueous solution of the catalysts is added at the start of step (b), the only water added being the water of the solution in which the catalyst is dissolved.

4. Process according to claim 1, wherein, at the start of step (a), the intermediate that is to be formed at the end of step (a) is added in an amount of less than 5% by weight.

5. Process according to claim 4, wherein said intermediate is added in an amount of less than 3% by weight.

6. Process according to claim 1, wherein the catalyst of step (a) belongs to the group consisting of the compounds of tungsten and molybdenum, particularly their acids and alkaline salts thereof.

7. Process according to claim 6, wherein said catalyst is present in an amount comprised between 0.03 and 2 wt % with respect to the derivative of the unsaturated fatty acid.

8. Process according to claim 7, wherein said catalyst is present in an amount comprised between 0.07 and 1.8 wt % with respect to the derivative of the unsaturated fatty acid.

9. Process according to claim 7, wherein said catalyst is present in an amount comprised between 0.08 and 1.5 wt % with respect to the derivative of the unsaturated fatty acid.

10. Process according to claim 1, wherein the catalyst of step (b) is selected from the group consisting of the compounds of cobalt.

11. Process according to claim 10, wherein said compounds of cobalt are selected from the group consisting of cobalt acetate, cobalt chloride and cobalt sulphate.

12. Process according to claim 11 wherein said compounds of cobalt are present in an amount comprised between 0.1 and 3 mol % with respect to the diol.

13. Process according to claim 11 wherein said compounds of cobalt are present in an amount comprised between 0.2 and 2 mol % with respect to the diol.

14. Process according to claim 11 wherein said compounds of cobalt are present in an amount comprised between 0.3 and 1.5 mol % with respect to the diol.

15. Process according to claim 10, wherein a catalyst selected from the group consisting of tungsten and molybdenum, and their acids and alkaline salts, is added to said catalyst of the group of the compounds of cobalt.

16. Process according claim 15 wherein said compounds of tungsten and molybdenum are added in an amount up to 2 mol % respect to the diol.

17. Process according to claim 1 wherein the oxidizing compound is hydrogen peroxide.

18. Process according to claim 17, wherein said hydrogen peroxide is present in aqueous solution in a concentration comprised between 30% and 70%.

19. Process according to claim 17, wherein said hydrogen peroxide is present in aqueous solution in a concentration comprised between 35% and 60%.

20. Process according to claim 17, wherein said hydrogen peroxide is present in aqueous solution in a concentration comprised between 40% and 49.9%.

21. Process according to claim 1, wherein both the steps (a) and (b) are carried out at a pressure <20 atm.

22. Process according to claim 21, wherein said pressure is <15 atm.

23. Process according to claim 22, wherein said pressure is <10 atm.

24. Process according to claim 23 wherein both the steps (a) and (b) are carried out at atmospheric pressure.

25. Process according to claim 1, wherein said derivative of said unsaturated fatty acid is a derivative of a mono-unsaturated fatty acid.

26. Process according to claim 25, wherein said derivative of said mono-unsaturated fatty acid is obtained by esterification of mixtures comprising the ones present in vegetable oils selected from the group consisting of soybean oil, olive oil, castor oil, sunflower oil, peanut oil, rape-seed oil, corn oil, and palm oil.

27. Process according to claim 25, wherein said mono-unsaturated fatty acid is selected from the group consisting of 9-tetradecenoic acid (myristoleic acid), 9-hexadecenoic acid (palmitoleic acid), 9-octadeceneoic acid (oleic acid), 12-hydroxy-9-octadeceneoic acid (ricinoleic acid), icosenoic acid (gadoleic acid), 13-docosenoic acid (erucic acid), 15-tetracosenoic acid (nervonic acid).

28. Process according to claim 25, wherein the carboxylic group of said derivative of unsaturated fatty acid is modified by means of reaction with an alcohol to form an ester.

29. Process according to claim 28, wherein said ester group comprises a C1-C9 alkyl group.

30. Process according to claim 29, wherein said ester group is selected from the group consisting of methyl, ethyl, propyl.

31. Process according to claim 28, wherein said modified unsaturated fatty acid is methyl oleate obtained by transesterification of methanol with the triglycerides contained in sunflower oil with a high content of oleic acid.

\* \* \* \* \*